United States Patent [19]
Davidson

[11] Patent Number: 5,496,359
[45] Date of Patent: Mar. 5, 1996

[54] ZIRCONIUM OXIDE AND ZIRCONIUM NITRIDE COATED BIOCOMPATIBLE LEADS

[75] Inventor: James A. Davidson, Germantown, Tenn.

[73] Assignee: Smith & Nephew Richards, Inc., Memphis, Tenn.

[21] Appl. No.: 112,587

[22] Filed: Aug. 26, 1993

Related U.S. Application Data

[63] Continuation-in-part of Ser. No. 919,932, Jul. 27, 1992, Pat. No. 5,282,850, which is a continuation-in-part of Ser. No. 830,720, Feb. 4, 1992, Pat. No. 5,258,022, which is a continuation-in-part of Ser. No. 819,348, Jan. 9, 1992, Pat. No. 5,152,795, which is a continuation-in-part of Ser. No. 385,285, Jul. 25, 1989, Pat. No. 5,037,438.

[51] Int. Cl.⁶ ..................................................... A61N 1/04
[52] U.S. Cl. ........................................................ 607/115
[58] Field of Search ............................ 128/642; 607/115, 607/116, 119, 121, 122, 129

[56] References Cited

U.S. PATENT DOCUMENTS

| | | |
|---|---|---|
| 2,987,352 | 6/1961 | Watson et al. . |
| 3,643,658 | 2/1972 | Steinemenan . |
| 3,677,795 | 7/1972 | Bokros et al. . |
| 3,685,059 | 8/1972 | Bokros et al. ............................. 623/2 |
| 3,969,130 | 7/1976 | Bokros ...................................... 623/2 |
| 4,040,129 | 8/1977 | Steinemann et al. . |
| 4,145,764 | 3/1979 | Suzuki et al. . |
| 4,159,358 | 6/1979 | Hench et al. . |
| 4,223,412 | 9/1980 | Aoyagi et al. . |
| 4,495,664 | 1/1985 | Blanquaert . |
| 4,514,589 | 4/1985 | Aldinger et al. ......................... 607/119 |
| 4,608,051 | 8/1986 | Reck et al. . |
| 4,617,024 | 10/1986 | Broemer et al. . |
| 4,652,459 | 3/1987 | Engelhardt . |
| 4,652,534 | 3/1987 | Kasuga . |
| 4,671,824 | 6/1987 | Haygarth ................................. 148/6.11 |
| 4,687,487 | 8/1987 | Hintermann . |

(List continued on next page.)

FOREIGN PATENT DOCUMENTS

| | | |
|---|---|---|
| 770080 | 10/1967 | Canada . |
| 1140215 | 1/1983 | Canada . |
| 38902 | 11/1981 | European Pat. Off. . |
| 0159410 | 12/1984 | European Pat. Off. . |
| 0410711A1 | 7/1990 | European Pat. Off. . |
| 2134926 | of 0000 | Germany . |
| 1943801 | 4/1970 | Germany . |
| 2811603 | 3/1978 | Germany . |
| 08939 | 4/1986 | Japan . |
| 180679 | 7/1986 | Japan . |
| 1325269 | 8/1973 | United Kingdom . |
| 2206182A | 5/1987 | United Kingdom . |

OTHER PUBLICATIONS

Davidson, et al., "Wear, Creep and Frictional Heating of Femoral Implant Articulating Surfaces and the Effect on Long–Term Performance—Part II, Friction, Heating, and Torque," *J. of Biomedical Materials Research: Applied Biomaterials,* vol. 22, No. A1, pp.

(List continued on next page.)

*Primary Examiner*—William E. Kamm
*Attorney, Agent, or Firm*—Pravel, Hewitt, Kimball & Krieger

[57] ABSTRACT

Cardiovascular, vascular, and percutaneous implants, as well as catheters and other surgical instruments, fabricated from a core or substrate of a low modulus metal coated with blue to black zirconium oxide or zirconium nitride. The coating provides enhanced thrombogenicity, biocompatibility, blood compatibility, corrosion-resistance, friction and microfretting resistance, durability, and electrical insulation, where applicable. The coatings may be applied to low modulus metallic substrates by physical or chemical vapor deposition as well as other ion-beam assisted methods. Preferably, however, for optimizing attachment strength, the implants and surgical instruments are fabricated from zirconium or zirconium-containing alloys and the coatings are formed by oxidizing or nitriding through an in situ method that develops a coating from and on the metal surface of the implant or instrument, without need for depositing a coating on the metal surface.

12 Claims, 3 Drawing Sheets

U.S. PATENT DOCUMENTS

| | | |
|---|---|---|
| 4,714,474 | 12/1987 | Brooks, Jr. et al. . |
| 4,728,488 | 3/1988 | Gillett et al. . |
| 4,778,461 | 10/1988 | Pietsch et al. .............................. 623/2 |
| 4,822,355 | 4/1989 | Bhuvaneshwar . |
| 4,834,756 | 5/1989 | Kenna . |
| 4,922,927 | 5/1990 | Fine et al. ................................ 607/122 |
| 4,945,342 | 7/1990 | Steinemann ............................. 607/116 |
| 4,955,911 | 9/1990 | Frey et al. . |
| 5,037,438 | 8/1991 | Davidson . |
| 5,061,278 | 10/1991 | Bicer . |

OTHER PUBLICATIONS

ASTM F86–84, "Standard practice for Surface Preparation and Marking of Metallic Surgical Implants," pp. 12–14 (1984), corrected editorially in May 1987.

Khruschov, "Principles of Abrasive Wear," Wear 28, 69–88 (1974).

Weightman and Light, "The Effect of the Surface Finish of Alumina and Stainless Steel on the Wear Rate of UHMW Polyethylene," *Biomaterials*, 7, 20–24 (1986).

Viegas, et al., "Metal Materials Biodegration: A Chronoamperometric Study," *J. of Materials Science: Materials in Medicine 1*, 105–109 (1990).

Briscoe, et al., "The Friction and Wear of High Density Polythene: The Action of Lead Oxide and Copper Fillers," *Wear* 27, 19–34 (1974).

Rabinowicz, "Lubrication of Metal Surface by Oxide Films," ASLE Translations, 10, 400–407 (1967).

Mausli, et al., "Constitution of Oxide on Titanium Alloys for Surgical Implants," *Advances in Bio Materials*, 8, p. 305 (1988).

Rokicki, "The Passive Oxide Film on Electropolished Titanium" (Feb. 1990).

Coll and Jacouot, "Surface Modification of Medical Implants and Surgical Devices Using TiN Layers," *Surface and Coatings Technology*, 36, p. 867 (1988).

Bradhurst and Heuer, "The Influence of Oxide Stress on the Breakaway Oxidation of Zircaloy–2," *J. of Nuclear Materials*, 37, p. 35 (1970).

Demizu, et al., "Dry Friction of Oxide Ceramics Against Metals: The Effect of Humidity," *Tribology Transactions*, 33, p. 505 (1990).

Bill, R. C., "Selected Fretting–Wear–Resistant Coatings for Ti–6%Al–%Allo" Wear 106 (1985), pp. 283–301.

Bertrand, G., et al., "Morphology of Oxyde Scales Formed on Titanium," vol. 21, *Oxidation of Metals*, Nos. 1/2 (1983), pp. 1–19.

More, R. B., Silver, M. D., "Pyrolytic Carbon Prosthetic Heart Valve Occluder Wear: In Vivo vs. In Vitro Results for the Bjork–Shiley Prosthesis," *Journal of Applied Biomaterials*, vol. 1, pp. 267–278 (1990).

Kowbel, W., et al., "Effect of Boron Ion Implantation on Tribological Properties of CVD $Si_3N_4$," vol. 46, *Lubrication Engineering*, 10 pp. 645–650.

Author Unknown, "Boric Acid: A self–replenishing solid lubricant," Tex Spotlight, Advanced Materials and Processes, pp. 40–42 (Jul. 1991).

"Increase in Biocompatibility of Polymers by Treatment with Phosphatidyl Choline," Study done by Biocompatibles, Ltd., U.K. and Wolfson Centre for Materials Technology Brunel University (Jul. 1991).

Golomb, G., et al., "Prevention of bioprosthetic heart valve tissue calcification by charge modification: Effects of protamine binding by formaldehyde," vol. 25, *J. of Biomedical Materials Research*, pp. 85–98 (1991).

Akins, Cary W., "Mechanical Cardiac Valvular Prostheses," Current Review by the Society of Thoracic Surgeons, pp. 161–172 (1991).

Haygarth and Fenwick, "Improved Wear Resistance of Zirconium by Enhanced Oxide Films," Thin Solid Films, Thin Solid Films, Metallurgical, and Protective Coatings, vol. 118, pp. 351–362 (1984).

"The Cementless Fixation of Hip Endoprosthesis," edited by Morscher, Mittelmeier, 'Total Hip Replacement with the Autophor Cement–Free Ceramic Prosthesis,' pp. 225–241 (1984).

Brown and Merritt, "Evaluation of Corrosion Resistance of Bioloy," Dept. of Biomedical Engineering, Case Western Reserve University, Feb. 13, 1986 (1:8).

O'Connor, Leo, "Novacor's VAD: How to Mend a Broken Heart," Mechanical Engineering, Nov. 1991 pp. 53–55.

Korane, Kenneth, "Replacing the Human Heart," Machine Design, Nov. 7, 1991, pp. 100–105.

Baruah Bileaflet Mechanical Cardioc Valve Prosthesis, "Instructions for Use" brochure (Author and date unknown).

Pamphlet, "Zircadyne Corrosion Properties," Teledyne Wah Change Albany (no date) pp. 1–16.

Conte, Borello, and Cabrini, "Anodic Oxidation of Zircaloy–2," Journal of Applied Electrochemistry, vol. 6, pp. 293–299 (1976).

Budinski, K. G., "Tribological Properties of Titanium Alloys," vol. 1, *Wear of Materials*, AMSE (1991) pp. 289–299.

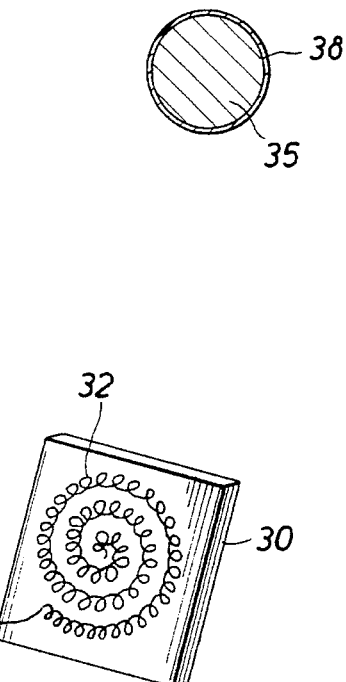
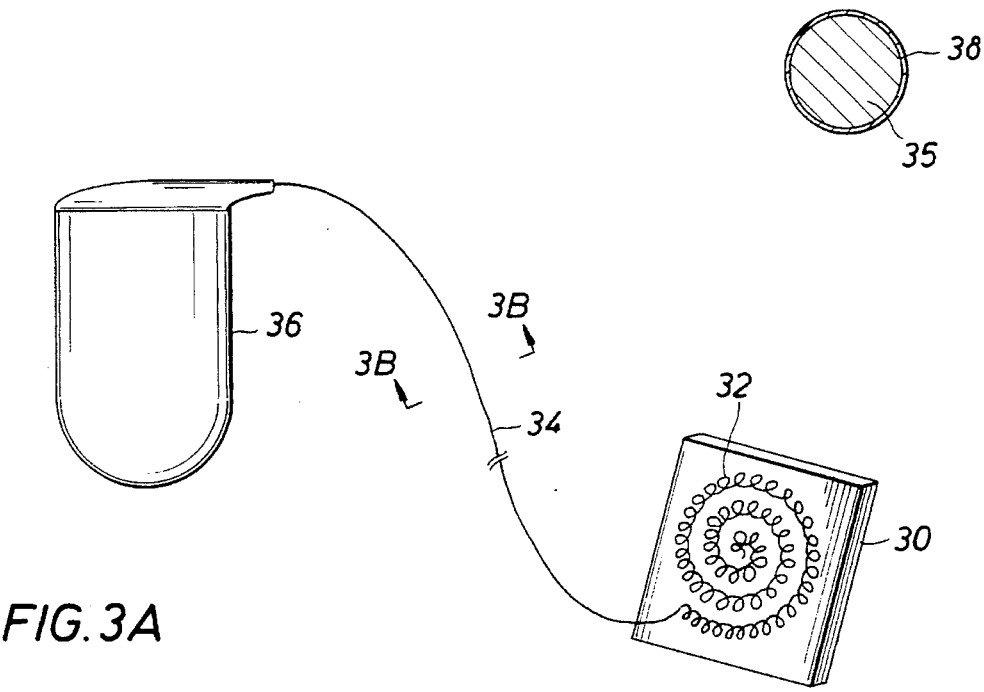
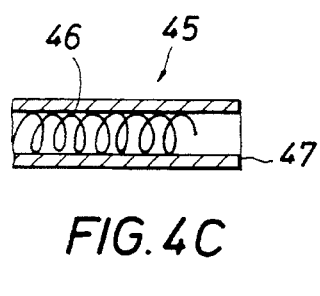
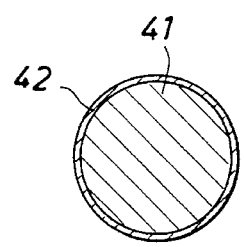
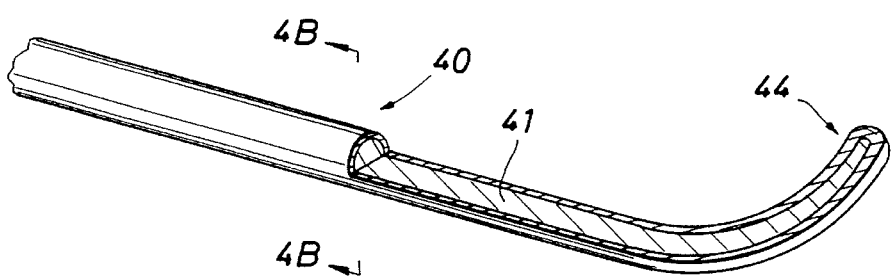

ZIRCONIUM OXIDE AND ZIRCONIUM NITRIDE COATED BIOCOMPATIBLE LEADS

RELATED APPLICATIONS

This application is a continuation-in-part of U.S. Ser. No. 919,932 filed Jul. 27, 1992 now U.S. Pat. No. 5,282,850, which is in turn a continuation-in-part of U.S. Ser. No. 830,720 filed Feb. 4, 1992 now U.S. Pat. No. 5,258,022, which is in turn a continuation-in-part of U.S. Ser. No. 819,348 filed Jan. 1, 1992 now U.S. Pat. No. 5,152,795, which is in turn a continuation-in-part of U.S. Ser. No. 385,285 filed Jul. 25, 1989 now U.S. Pat. No. 5,037,438.

BACKGROUND OF THE INVENTION

1. Field of the Invention

The invention is of cardiovascular, vascular, leads, catheters, and percutaneous implants of enhanced biocompatibility, blood compatibility, and corrosion resistance, as well as surgical instruments of superior low friction, flexibility, and corrosion characteristics. More specifically, the invention implants and instruments are fabricated from relatively low modulus metals, such as zirconium or a zirconium-containing alloy, and are coated with blue to black zirconium oxide or zirconium nitride to provide enhanced blood compatibility, microfretting resistance, electrical insulation, and corrosion resistance where applicable.

2. Description of the Related Art

With advances in the technology for treating heart diseases, there has developed an increasing demand for sophisticated cardiovascular implants and surgical tools for use in cardiovascular surgery.

For example, vascular grafts are used to replace damaged blood vessels. These grafts may be fabricated from biocompatible organic polymers, such as woven dacron, silicone, polyurethane, and the like. Others are not of woven polymers, but are simply smooth cylindrical tube sections (i.e., allographs or autographs) that replace the section of removed artery or vein. While these grafts are fabricated from biocompatible polymers, it is frequently desirable to have a graft fabricated from a blood compatible metal that will retain its shape, not degrade with time, and not collapse under exerted pressure. While the buildup of a coating of certain blood components (such as endothelial cells) that provide a surface compatible with blood is desirable, the metal should desirably be resistant to a build up of adverse blood components on the graft surface which might ultimately impede the flow of blood through the graft.

It is currently known to use balloon-expandable stents to prop open blood vessels that have become damaged so that they are prone to collapse, or blood vessels that have become coated on the inside with plaque, thereby impeding the flow of blood. Typically, these stents are inserted by means of a guide wire with a stent in a collapsed state at its distal end. Once the stent is in position, a balloon positioned inside the stent is inflated so that the stent expands and props open the desired area of the blood vessel. Such stents are also used for gastrointestinal, urinary, and other non-cardiovascular applications.

Certain cardiac treatment procedures also require the use of pacemaker leads and other current-bearing leads that are usually coated with an insulative barrier that both electrically insulates and isolates the current-bearing core from body fluids. Currently, a typical pacemaker or other cardiovascular lead includes a central core of electrically conductive metal, usually cobalt-nickel alloy, coated with a polymeric insulative coating, usually polyurethane. However, polyurethane coatings eventually break down under the effect of body fluids and enzymes producing potentially harmful degradation products. Further, the polymer coating may crack or separate with time so that body fluids or adjacent wires come in contact with the electrical conductor and interfere with electrical signals. Further, the electrical conductor is then subject to corrosion due to body fluids.

In a typical defibrillator, a flexible silicone polymeric patch with a thinly coiled titanium, cobalt-nickel, or stainless steel wire is attached to the appropriate segment of heart muscle. A lead wire is attached to this coil for powering the coil to stimulate the heart muscle. The lead wire exits from the body to an external power source. The lead wire is frequently coated with polyurethane. Thus, this lead wire is both an electrical carrying device and a percutaneous device, in the sense that it penetrates the skin and exits from the body. However, it is coated with a relatively soft and fragile polymeric composition which provides limited protection to potential damage to lead sections carried outside the body. Thus, there is a need for a percutaneous lead that is crush resistant, biocompatible, and that provides suitable electrical conductance and insulation to isolate the electrical carrying lead from other lead wires and body tissue. Further, the lead should be resistant to chemical degradation in body fluids.

During surgery, guide wires may be inserted into blood vessels. These guide wires may be used to locate sensors, stents, leads, and other devices in specific areas, or may be equipped with cutting edges at their tips so that blood vessels may be surgically cleared of obstructions. In one of the commercially available guide wires, the wire includes a central core made of an elastic metallic alloy coated with a polyurethane jacket which is in turn coated with a hydrophilic material. This meets at least some of the requirements for a suitable guide wire, these requirements being that the exterior of the guide wire in contact with blood vessel tissue be of low friction with respect to the blood vessels, and that the guide wire be kink-resistant and flexible (low modulus) for maneuverability within the blood vessel. Also, the exterior surface of the guide wire in contact with the interior surface of a catheter (the catheter walls) should have low friction relative to the catheter wall material. Further, the guide wire should be radiopaque, to allow the surgeon to track the position of the guide wire within the blood vessel. Finally, the construction of the guide wire should be such as to allow adequate torque control, desirably so that one rotation at a control end of the guide wire leads to one rotation at the cutting edge tip of the guide wire. There yet exists a need for improved guide wires that can meet all these requirements and, additionally, have a high surface hardness to improve cutting edge sharpness and cutting edge durability.

SUMMARY OF THE INVENTION

The invention provides improved cardiovascular implants and cardiovascular surgical instruments fabricated from a low modulus metallic material, such as zirconium and zirconium-containing alloys, covered with a biocompatible, microfretting and corrosion-resistant, hemocompatible, electrically insulative coating of blue to black zirconium oxide or yellow to orange zirconium nitride. These coatings are tightly adherent to the underlying metal and are of a sufficient thickness to provide the desired electrical insulation, blood compatibility, microfretting resistance, and corrosion resistance, as may be required for the particular cardiovascular implant or surgical tool (i.e., guide wires or sensors).

In one embodiment, the invention provides a vascular graft fabricated from a low modulus metallic composition, such as zirconium or zirconium-containing alloys, coated predominately with blue to black zirconium oxide or zirconium nitride. This coated graft provides enhanced biocompatibility and hemocompatibility, while at the same time providing enhanced crush resistance and long life when compared with grafts fabricated from biocompatible polymeric compositions, such as polyurethane or dacron. While the graft may be fabricated from tubular sections of low modulus metallic compositions coated with zirconium oxide or nitride, the graft may also be fabricated from woven wire fabricated from these low modulus metallic compositions. The coating of blue to black zirconium oxide or zirconium nitride may be applied by any of a number of processes including physical vapor deposition (PVD) and chemical vapor deposition (CVD) but preferably by a process of in situ oxidation or nitridation.

In another embodiment, the invention provides balloon-expandable stents fabricated from low modulus metals coated with blue to black zirconium oxide or zirconium nitride. These stents are generally used temporarily or permanently to prop open tubular conduits with the body, such as blood vessels, urinary tract, gastrointestinal tract, and the like. The stents may be positioned within a blood vessel, for example, using conventional balloon-expanding tools, and may then be expanded into position to prop open the walls of the blood vessel. The blue to black zirconium oxide or yellow to orange zirconium nitride coatings provide highly hemocompatible and biocompatible surfaces in contact with blood vessel walls and blood thereby minimizing adverse blood reaction and build up of thrombus or other adverse blood components on the stent. Thus, the invention coated stent reduces the likelihood of thrombus build up on its surface which might subsequently require further surgery to clear any developing blockage. The stents of the invention also provide corrosion resistance which is an important consideration, particularly for gastrointestinal and urinary applications.

In another embodiment, the invention provides electrical signal carrying leads for use in a living body. These leads carry a signal from a source, sometimes external to the body, to or from an organ, such as the heart, to provide a therapeutic effect. Alternatively, for diagnostic applications, a signal may be carried by a sensor from an organ of the body to an external device for recording the signal or for otherwise using the signal. Thus, the invention provides, for instance, sensor, pacemaker, and defibrillator leads that are ductile and of high strength while providing biocompatibility, blood compatibility, and resistance to corrosion in body fluids. These pacemaker, sensor, and defibrillator leads include a central core of a low modulus electrically conductive metallic composition, such as zirconium or zirconium-containing alloys, covered with an electrically insulative, abrasion-resistant coating that is tightly adherent to the core. These coatings are resistant to corrosion by body fluids so that their useful life exceeds that of polyurethane coated leads which are subject to corrosion and degradation by body fluids with subsequent interference with electrical signals. The invention also provides numerous other electrical signal bearing leads coated with blue to black zirconium oxide or zirconium nitride.

In another embodiment, the invention provides percutaneous devices fabricated from low modulus alloy metallic compositions, such as zirconium and zirconium-containing alloys, that have enhanced biocompatibility, hemocompatibility, durability, stability, and crush resistance as compared to conventionally used biocompatible polymeric compositions. The invention percutaneous devices may also have surfaces covered with a coating of blue to black zirconium oxide or yellow to orange zirconium nitride to provide enhanced biocompatibility, hemocompatibility, durability, and abrasion resistance.

The invention also provides surgical tools, such as guide wires and catheters, fabricated from a low modulus metallic composition, such as zirconium or zirconium-containing alloys, coated with a tightly adherent coating of blue to black zirconium oxide or zirconium nitride. These guide wires are radiopaque, of low friction when in contact with body tissue, particularly blood vessel tissue, kink-resistant but flexible due to the low modulus of the metallic core and relative flexibility of the hemocompatible, biocompatible, and abrasion-resistant zirconium oxide or nitride coating.

Furthermore, the oxide- or nitride-coated surfaces according to the invention may be coated with other compositions to further enhance biocompatibility and performance. For example, phosphatadyl choline, heparin, proteins, or other surface treatment may be applied for reducing platelet adhesion or other adverse cellular or tissue response to surfaces in contact with blood, or boronated or silver-doped hardened surface layers to reduce friction and wear if the implant is subject to microfretting or other mechanical wear. In certain instances, it may be desirable to coat the surfaces according to the invention with a medicament such as an antibiotic, anticoagulant, and the like, as needed for the particular application.

The thickness of the hard zirconium oxide or nitride coating is preferably less than about 5 microns (i.e., in the range about 3 to about 6 microns) for optimal residual compressive stresses and minimal dimensional changes or distortion during oxidation or nitridation. However, the thickness of the coating is frequently not critical, for instance in the case of vascular grafts and lead wires where the surface coating provides enhanced hemocompatibility and biocompatibility and is not subject to forces requiring optimal residual compressive stresses. Thus, in these cases, the thickness of the coating is limited only by its own integrity, i.e., that it is not subject to cracking and spalling, thereby potentially releasing particulates into the body of the patient. Such coatings may range from about 0.1 to about 20 microns or more in thickness.

BRIEF DESCRIPTION OF THE DRAWINGS

A better understanding of the present invention can be obtained when the following detailed description of the preferred embodiment is considered in conjunction with the following drawings, in which:

FIG. 3A is a schematic diagram of the components of a defibrillator, showing power source, lead wire, and polymeric patch with coiled electrode.

FIG. 3B is a cross-section (coating exaggerated in dimension to show detail) of the lead wire of FIG. 3A.

FIG. 4A is a schematic diagram, in partial cross section, of the distal end of a guide wire showing a central core of low modulus metal covered with a coating (exaggerated in thickness to show detail) of blue to black zirconium oxide or zirconium nitride.

FIG. 4B is a schematic cross-section of coated guide wire with coating shown in exaggerated thickness.

FIG. 4C is a partial schematic showing a catheter of coiled metal wire construction in an encasing polymeric sheath.

DETAILED DESCRIPTION OF THE PREFERRED EMBODIMENTS

The invention provides low modulus metallic cardiovascular, catheter, and percutaneous implants and surgical instruments coated with a layer of blue to black zirconium oxide or zirconium nitride. These coatings provide a blood compatible, microfretting resistant, electrically insulative, stable, and corrosion resistant ceramic coating. Furthermore, these ceramic blue to black zirconium oxide or zirconium nitride coatings may be further overlaid with a thin coating of phosphatadyl choline, heparin, or other surface treatment for further reducing platelet adhesion, if the implant or surgical instrument will be in contact with blood. Other medicaments may also be coated onto the ceramic surfaces of the invention. The ceramic coatings of the invention may also be modified by boronation or silver doping to further improve friction and wear characteristics, if necessary.

The term "low modulus" as used to describe the metallic compositions preferred in this invention include those metallic compositions that preferably have a modulus of elasticity less than about 130 GPa.

The term "blue to black" as used to describe zirconium oxide means that the color of the oxide may range from blue to black, depending on zirconium concentration in the oxidized alloy or process conditions that produce the coating. Thus, for pure zirconium, the blue to black oxide formed by the preferred in situ process is substantially monoclinic zirconium oxide. However, if a zirconium alloy is used, then, for the useful zirconium alloys, the in situ process will produce a surface containing a mixture of oxides, but still substantially zirconium oxide, to produce the blue to black appearance. If an ion beam deposition assisted or other non-in situ process is used, such as chemical or vapor deposition, then the color of the oxide is not affected by the substrate metal. In this case, the white tetragonal or cubic $ZrO_2$ is possible as well. Such coatings are useful as "overlay" coatings on an in situ blue-black zirconium oxide or yellow-orange zirconium nitride coating. Since the hardness match between such overlays and the in situ coatings are closer than between overlay and substrate metal, the coatings are more firmly attached and have superior integrity. Other hard coatings are also useful as overlays—such as amorphous diamond-like carbon coatings, wear-resistant coatings formed by silver deposition, and lubricious boronated coatings.

The term "yellow to orange" as applied to zirconium nitride refers to the range of colors of zirconium nitride and the comments above about alloys and consequent mixtures of oxides with zirconium oxide also apply in the nitride context.

Figure 1:
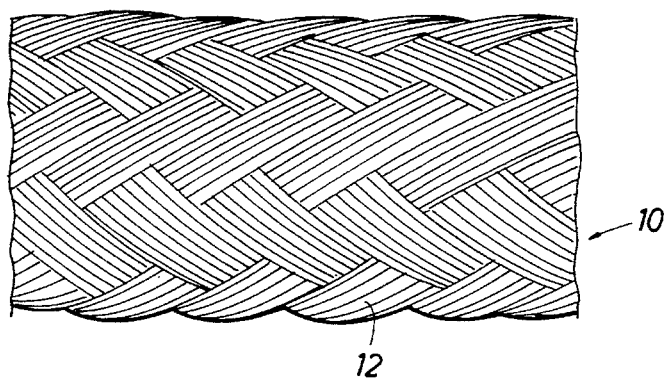
FIG. 1 is a schematic diagram of a vascular graft of woven low modulus metallic composition coated with blue to black zirconium oxide or zirconium nitride.

FIG. 1 shows a side view of a substantially tubular vascular graft 10, with bore therethrough, made of woven low modulus metallic wires 12 coated with blue to black zirconium oxide or zirconium nitride. While the graft shown is made of woven wires of a low modulus metal, such as zirconium or zirconium-containing alloys, the graft can also be fabricated from a cylindrical tubing of low modulus metal, coated with blue to black zirconium oxide or zirconium nitride. As explained before, since the coating surface provides the desired thrombogenicity and hemocompatibility, the thickness of the coating is not critical other than that it should be dense and well-attached to the substrate. However, it is preferred that the coating thickness range from about 0.1 to about 20 microns, more preferably from about 1 to about 10 microns, most preferably about 3–6 microns.

Figure 2A:
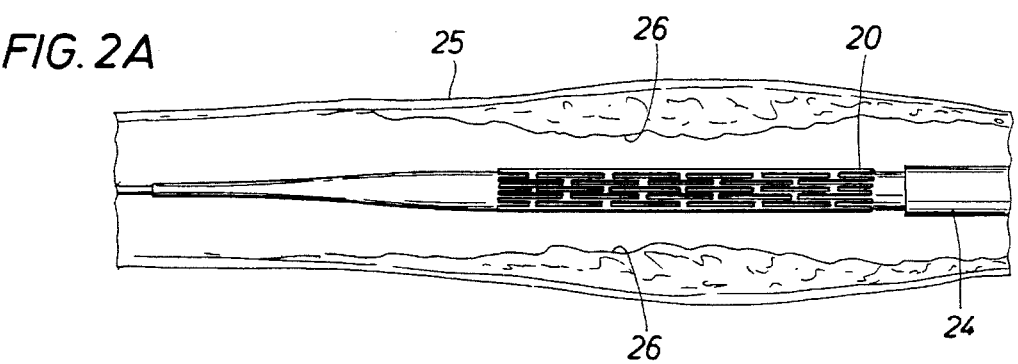
FIG. 2A is a schematic diagram showing a balloon expandable stent, according to the invention, positioned within a segment of a blood vessel to be propped open.
Figure 2B:
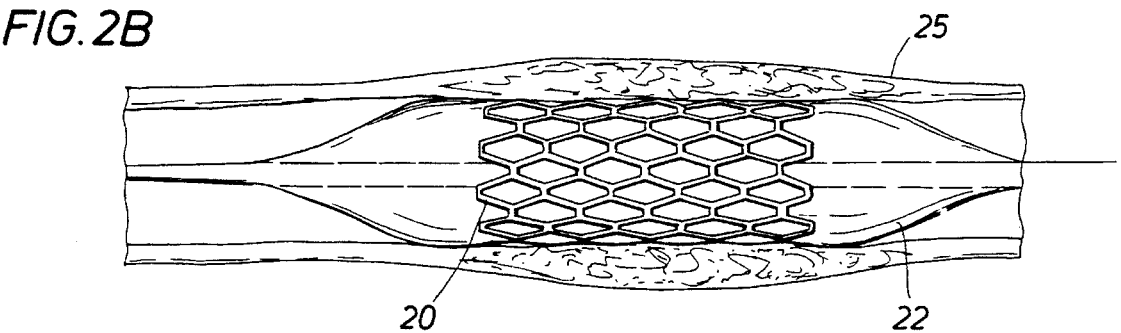
FIG. 2B is a schematic diagram showing a balloon expanding a stent into position within a blood vessel.
Figure 2C:
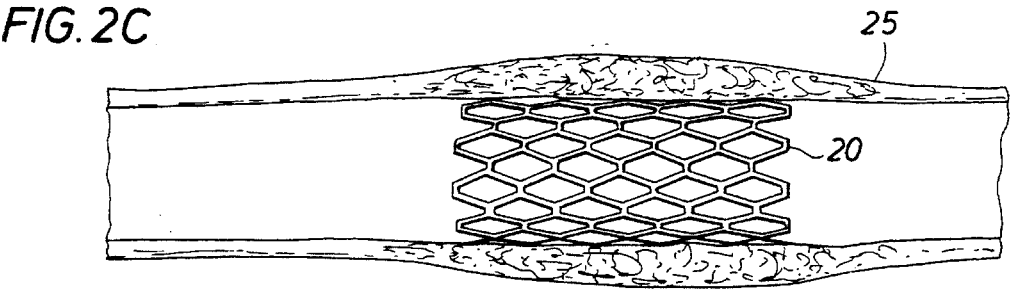
FIG. 2C is a schematic diagram of a stent, according to the invention, in place in a blood vessel.

FIG. 2A shows an expandable stent 20, in non-expanded state, positioned on the distal end of a balloon expandable segment 22 of a guide wire 24. The stent is fabricated from a low modulus metal, such as zirconium or zirconium-containing alloy, and is fabricated so that it can be collapsed over a balloon segment of a balloon catheter. When the stent is in position, within a tubular conduit in the body such as a segment of blood vessel, for example, to be propped open, the balloon is expanded, as shown in FIG. 2B, thereby expanding the stent radially outward up to the blood vessel wall 26 so that means for gripping soft tissue, such as barbs (not shown), on the outer surface of the stent engage and grip blood vessel tissue to anchor the stent in position. In this way, the blood vessel is permanently propped open as shown in FIG. 2C. The invention blue to black zirconium oxide or yellow to orange zirconium nitride coatings provide a blood compatible low friction surface to which platelets and other adverse blood-borne compositions will not tend to adhere thereby preventing build up of adverse tissue and subsequent blockage of the propped open blood vessel. Again, the thickness of the coating may range from about 0.1 to about 20 microns, preferably about 1 to about 10 microns, most preferably about 3–6 microns.

FIG. 3A shows a defibrillator including a flexible silicone polymeric patch 30 with a coil of conductive wire 32 (typically titanium, stainless steel, or cobalt-nickel-chromium) on the side of the silicone patch 30 that will contact muscle tissue. When in place in the body, the lead wire 34 that carries power to the coil 32 extends out of the body (through the skin) and is electrically connected to a power source in a protective container 36. According to the invention, the lead wire 34 is fabricated with an electrically conductive core 35 of low modulus metal, preferably zirconium or zirconium-containing alloys, and has a coating 38 of blue to black zirconium oxide or zirconium nitride. This coating, shown in exaggerated scale in FIG. 3B, electrically insulates the lead wire from electrical contact with surrounding body tissue while also protecting the metallic core from corrosion and attack by body fluids. Thus, because the invention ceramic coatings are stable, inert, and more resistant to, attack and degradation, than the currently used polymeric coatings, the lead wire has potentially longer life and is also more biocompatible, in that it does not spall or degrade with time, like polyurethane or other polymer coatings, that may interfere in a potentially harmful way with desired electrical signals.

FIG. 3B is a cross-section of the lead wire 34 showing the core of low modulus metal 35 and the thin coating of ceramic zirconium oxide or nitride 38 (thickness exaggerated to show detail). The thickness of the coating may range from 0.1 to about 20 microns or more, more preferably from about 1 to about 10 microns, most preferably about 3–6 microns.

FIG. 4A shows, in partial cross section, the distal end of a guide wire 40 fabricated according to the invention. The guide wire has a core 41 of low modulus metal, preferably zirconium or zirconium-containing alloy, coated with a layer of hard, dense, blue to black zirconium oxide or zirconium nitride 42, as shown in FIG. 4B. In this case, the guide wire is equipped with a cutting tip 44, also coated with blue to black zirconium oxide or zirconium nitride to provide a sharp, hard, wear-resistant cutting edge. Further, because of the hard dense ceramic zirconium oxide or nitride surface layer, the guide wire is kink-resistant and provides good torque control in that one rotation at a control end leads to a similar rotation at the cutting end. The coatings, as explained before, are of low friction, wear resistant, hemocompatible and thrombo-resistant. Since the guide wire is fabricated of metal and ceramic, it is highly visible under X-rays, providing excellent radiopacity. The coatings may be from about 0.1 to about 20 microns or more thick, preferably about 1 to about 10 microns thick, most preferably about 3–6 microns thick. These coatings may also beneficially be applied to cutting edges of the guide wires. Such hard surface cutting edges have long life and do not adhere with tissue due to their low friction characteristics.

FIG. 4C shows a catheter 45 according to the invention through which a guide wire, or other device, may be utilized. For guide wire applications, the internal catheter construct for guiding a wire or other apparatus is a solid thin tube of low modulus alloy, or a coiled low modulus alloy wire 46, encased in a polymer sleeve 47. A hard oxide or nitride ceramic surface layer over the surfaces of the low modulus alloy construct 46 provides a low friction surface to aid in insertion and control of a guide wire. The hard ceramic surface layer produces a lower friction, lower torque condition over existing metal-catheter wall materials combinations.

Figure 5A:
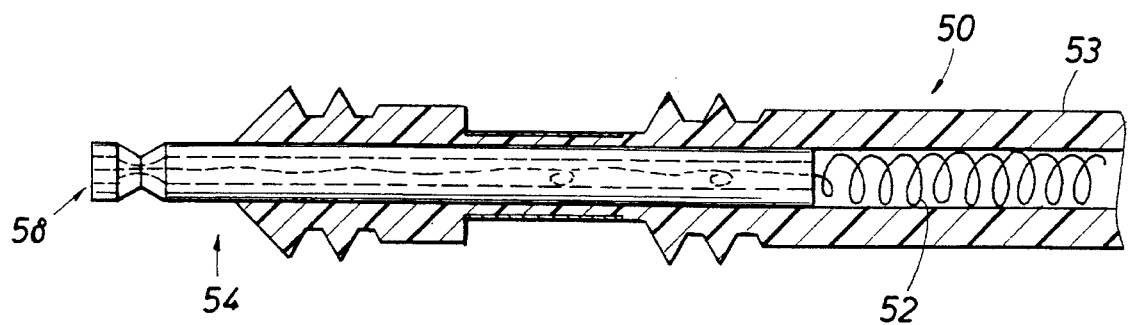
FIGS. 5A–C are schematic diagrams of a prior art pacemaker lead with polyurethane covering and "screw-in" design electrodes for attaching to the heart.
Figure 5B:
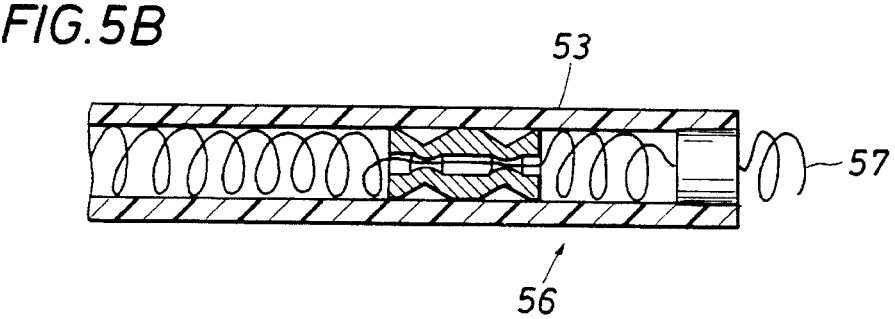
Figure 5C:
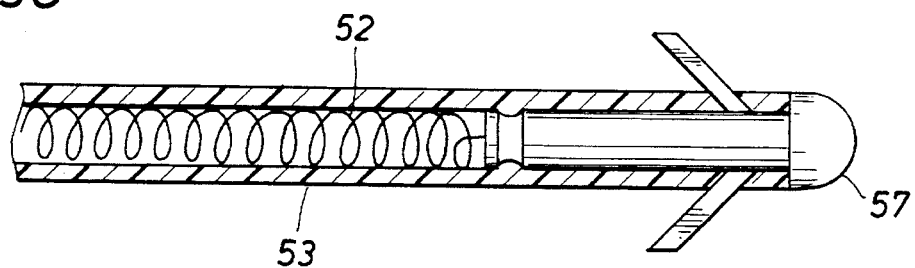

Pacemaker leads are manufactured by several corporations, including Medtronic, which produces a range of pacemaker lead designs. Two of these designs are shown in schematic form in FIGS. 5A–C. The pacemaker lead body 50 has a centrally disposed metallic conductor 52 typically made of cobalt-nickel alloy, such as MP35N®. This conductor 52 is usually made up of several strands of coiled wire, each having a diameter of about 0.15–0.20 mm. The conductor 52 is covered by an insulative, protective sheath 53 so that the elongate body 50 of the pacemaker lead has an overall diameter ranging from about 2.2 to about 3 mm. The pacemaker has a first end 54 with an electrode 58 for contacting with a matching electrode on a pulse generator (not shown); and a second end 56 with an electrode 57 for contacting heart muscle. As supplied, these two ends are covered with protective polyurethane caps which can be removed for installation of the pacemaker. In order to prevent electrical interference with the conductor 52, a polymeric insulative sleeve 53 is disposed over the entire pacemaker lead body 50, with the exception of the exposed electrodes 57 for contacting heart muscle and the contact electrode 58 for engaging with the pulse generator that houses the electronics and power pack for the pacemaker. As explained before, the organic polymeric sheath compositions, typically polyurethane, slowly degenerate in the body causing problems, not only due to potential deterioration of electrical insulation and interference with electrical signals but also because of potentially toxic products of degradation.

Figure 5D:
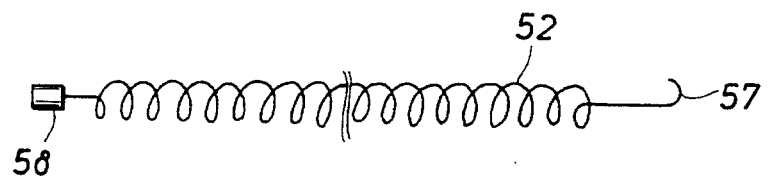
FIG. 5D is a schematic of an embodiment of the invention coated pacemaker leads.

The invention provides, as shown schematically in FIG. 5D, a pacemaker wherein the conductor 52, comprising either a single wire or multiple wires, is fabricated from a low modulus metallic alloy that is coated with blue to black zirconium oxide or yellow to orange zirconium nitride, with the exception of the electrode for contacting heart muscle 57, and an optional electrode 58 at the other end of the lead for engaging the pulse generator: exposed low modulus metallic ends of the wire or wires are preferably connected directly to a pulse generator thereby avoiding the necessity for a weld or crimp to attach an electrode 58 to the conductor 52, which crimp may result in local galvanic corrosion or physically weakened regions. Further, since the zirconium and nitride coatings provide a natural protective insulative surface, the use of a coiled construct could be avoided by using only a preferred single-strand, non-coiled low modulus metallic wire construct for the conductor 52. This will also eliminate the need for a stiff guide wire, which is generally used to position the contacting electrode to the heart. Finally, if a single, non-coiled wire construct is used, the overall diameter of the pacemaker lead body 50 could be reduced considerably from the range of about 2.2–3 mm for commercially available leads to about 0.2–1 mm.

The pacemaker leads may be coated to a thickness ranging from about 0.1 to about 20 or more microns, more preferably about 1 to about 10 microns, most preferably about 3 to about 6 microns.

While the oxide and nitride coatings of the invention can be applied by various coating methods, in situ coating is preferred. These in situ methods require that the metal composition be zirconium or its alloys so that the coating can be formed by oxidizing or nitriding the metal itself, not by depositing zirconium oxide or nitride on the metallic surface by coating deposition methods. Thus, the in situ methods include oxidation or nitridation in air, oxygen (oxidation), nitrogen (nitridation), and salt baths. These methods are described below.

In order to form continuous and useful zirconium oxide or nitride coatings over the surface of zirconium alloys by an in situ method, the alloy should contain from about 50 to about 100 wt. % zirconium, preferably 80 to 100 wt. %. Common alloying elements include niobium, tantalum, and titanium, with often times the presence of hafnium. Yttrium may also be alloyed with the zirconium to enhance the formation of a tougher, yttria-stabilized zirconium oxide coating during the oxidation of the alloy. During oxidation, the protective surface layer will contain various amounts of zirconium oxide depending on the alloy composition. The greater the level of zirconium oxide, the darker (tending to black) the ceramic oxide appearance. However, this appearance may be blue for alloys with relatively lower levels of zirconium or for thinner oxide layers. For $ZrO_2$ surface oxides, the monoclinic structure is stable at room temperature and is black in appearance. However, higher temperature oxide structures such as cubic or tetragonal can range from grey to white. While zirconium and zirconium alloys may be custom-formulated by conventional methods known in the art of metallurgy, a number of suitable alloys are commercially available. These commercial alloys include among others Zircadyne 705, Zircadyne 702, and Zircalloy, Ti—Zr and Ti—MO—Zr alloys. Ti—Nb—Zr alloys are disclosed in U.S. Pat. No. 5,169,597, entitled "Biocompatible Low Modulus Titanium Alloy for Medical Implants" (hereby fully incorporated by reference) and are the preferred low modulus metals. It should be understood that other low modulus metallic compositions not containing zirconium may also be used if the coating is applied by other than in situ methods, e.g., chemical vapor deposition, physical vapor deposition.

To fabricate the coated article by an in situ process, the appropriate substrate is first produced and then subjected to process conditions which cause the natural (in situ) formation of a tightly adhered, diffusion-bonded coating of essentially zirconium oxide on its surface. The process conditions include, for instance, oxygen-containing gas, steam, or water oxidation or oxidation in a fluidized or salt bath. These processes ideally provide a dense, blue to black, hard, low-friction, wear-resistant zirconium oxide film or coating of thicknesses typically less than several microns ($10^{-6}$ meters) on the surface of the prosthesis substrate. In some instances, the zirconium-containing oxide coating can be as thin as 0.1–0.2 microns and still provide useful protection. Typically, below this coating, there is a zone wherein diffused oxygen from the oxidation process increases the hardness and strength of the underlying substrate metal, and optimizes coating durability and attachment strength.

Unlike the prior art titanium oxides of, for example, Steinemann's U.S. Pat. No. 3,643,648, in the preferred in situ oxidation method the oxygen supplied to form the blue, blue to black, zirconium oxide coatings of the invention is also a beneficial alloying component which improves the immediate substrate metal hardness, which in turn improves oxide attachment strength and durability and also improves the base-metal strength. Thus, the fatigue strength of the underlying zirconium metal is improved, thereby increasing the potential life of the prosthesis. In contrast, oxidation of titanium alloys tends to form multiple oxides of titanium, which are less well attached to the metal substrate, and importantly, stabilizes the lower strength α-phase which significantly reduces the metal's fatigue strength.

The air, oxygen, steam, and water oxidation processes are described in now-expired U.S. Pat. No. 2,987,352 to Watson, the teachings of which are incorporated by reference as though fully set forth. The air oxidation process provides a firmly adherent black, blue-black, or blue layer of essentially zirconium oxide ($ZrO_2$) of mainly monoclinic crystalline form, depending upon specific conditions of oxygen and water vapor levels during the process. If the oxidation process is continued to excess, the coating will whiten and tend to separate from the metal substrate. An in situ oxidation step may be conducted in either oxygen, air, steam, hot water, salt baths or fluidized beds. For convenience, the metal prosthesis substrate may be placed in a furnace having an oxygen-containing atmosphere (such as air) and typically heated at 700°–1100° F. up to about 6 hours. However, other combinations of temperature and time are possible. When higher temperatures are employed, the oxidation time should be reduced to avoid the formation of a less-adherent oxide.

It is preferred that, a blue-black zirconium oxide layer ranging in thickness from less than one micron up to about 6 microns should be formed, although thicker coatings ranging from about 1 to about 20 microns are also useful. For example, furnace air oxidation at 1000° F. for 3 hours will form an oxide coating on Zircadyne 705 about 3–4 microns thick. Longer oxidation times and higher oxidation temperatures will increase this thickness, but may compromise coating integrity if thickness exceeds about 20 microns. For example, one hour at 1300° F. will form an oxide coating about 14 microns in thickness, while 21 hours at 1000° F. will form an oxide coating thickness of about 7 to about 9 microns. Of course, because only a thin oxide is necessary on the surface, only very small dimensional changes, typically less than 10 microns over the thickness of the prosthesis, will result. In general, thinner coatings (up to about 6 microns) have better attachment strength, and more favorable residual surface stresses.

One of the salt-bath methods, also considered in situ methods, that may be used to apply the zirconium oxide coatings to the metal alloy prosthesis, is the method of U.S. Pat. No. 4,671,824 to Haygarth, the teachings of which are incorporated by reference as though fully set forth. The salt-bath method provides a similar, slightly more abrasion resistant blue to black zirconium oxide coating. The method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt. %. The addition of sodium carbonate lowers the melting point of the salt. As in air oxidation, the rate of oxidation is proportional to the temperature of the molten salt bath and the '824 patent prefers the range 550°–800° C. (1022°–1472° F.). However, the lower oxygen levels in the bath produce thinner coatings than for furnace air oxidation at the same time and temperature. A salt bath treatment at 1290° F. for 4 hours produces an oxide coating thickness of roughly 7 microns. Residual contaminants in the salt bath may be inadvertently left on the treated implant surface and produce adverse clinical results. While some of these may be removed by polishing and washing, it is nonetheless preferred to use the gas (air) oxidation/nitridation processes which provides less possibility of contamination by other elements.

Whether air oxidation in a furnace, in a fluidized bed, or salt bath oxidation is used, the zirconium oxide coatings are quite similar in hardness. For example, if the surface of a wrought Zircadyne 705 (Zr, 2–3 wt. % Nb) prosthesis substrate is oxidized, the hardness of the surface shows a dramatic increase over the 200 Knoop hardness of the original metal surface. The surface hardens of the blue-black zirconium oxide surface following oxidation by either the salt bath or air oxidation process is approximately 1700–2000 Knoop hardness.

In situ air or oxygen oxidation is the preferred method for producing the invention oxide coatings because it minimizes the potential for surface contamination, and allows oxygen diffusion into the metal substrate thereby allowing the formation of a tightly adherent oxide coating while also strengthening the zirconium or zirconium alloy metal substrate.

While the above discussion has dealt mainly with blue to black zirconium oxide coatings on prostheses, zirconium nitride (yellow-orange) coatings are also effective in reducing wear on opposing surfaces and preventing corrosion of the underlying substrate by body fluids.

Even though air contains about four times as much nitrogen as oxygen, when zirconium or zirconium alloy is heated in air as described above, the oxide coating is formed in thermodynamic preference to the nitride coating. This is because the thermodynamic equilibrium favors oxidation over nitridation under these conditions. Thus, to form an in situ nitride coating the equilibrium must be forced into favoring the nitride reaction. This is readily achieved by elimination of oxygen and using a nitrogen or ammonia atmosphere instead of air or oxygen when a gaseous environment (analogous to "air oxidation") is used.

In order to form an in situ zirconium nitride coating of about 5 microns in thickness, the zirconium or zirconium alloy prosthesis should be heated to about 800° C. for about one hour in a nitrogen atmosphere. Thus, apart from the removal of oxygen (or the appropriate reduction in oxygen partial pressure), or increasing the temperature, conditions for forming the zirconium nitride coating do not differ significantly from those needed to form the blue to black zirconium oxide coating. Any needed adjustment would be readily apparent to one of ordinary skill in the art.

When a salt bath method is used to produce an in situ nitride coating, then the oxygen-donor salts should be replaced with nitrogen-donor salts, such as, for instance, cyanide salts. Upon such substitution, a nitride coating may be obtained under similar conditions to those needed for obtaining an oxide coating. Such modifications as are necessary may be readily determined by those of ordinary skill in the art.

Alternatively, the zirconium oxide or nitride may be deposited onto the zirconium or zirconium alloy surface via other techniques than the in situ gaseous and salt bath methods described above. These methods encompass, for example, standard physical or chemical vapor deposition methods, including those using an ion-assisted deposition method. Techniques for producing such an environment are known in the art.

As in the case of the zirconium oxide coatings, the nitride coatings are useful even at thicknesses as low about 0.1 micron. However, thicknesses from about 1 to about 20 are preferred and the range about 3 to about 6 microns is most preferred.

If desirable in the particular application, the zirconium oxide or nitride coated article may be further coated by silver doping or boronation to improve wear-resistance. Additionally, amorphous diamond-like carbon, or other hard, biocompatible coatings may also be applied to either the base low modulus metal or to the oxidized or nitrided surface layer. When deposited over the hard oxide or nitride surface layer, amorphous diamond-like carbon and other types of hard overlay coatings will have improved attachment strength due to a closer hardness match than that between such coatings and relatively softer metal surfaces.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. A biocompatible lead for conducting electrical signals to or from an organ in a living body, the lead comprising;

an elongate flexible body having distal and proximal ends, the flexible body comprising:

(a) an electrically conductive core of low elastic modulus metallic composition for carrying the electrical signals; and (b) a corrosion-resistant, biocompatible, durable, stable coating selected from the group consisting of zirconium oxides, ranging in color from blue to black, and zirconium nitrides, ranging in color from yellow to orange; said coating disposed on surfaces of the core exposed to body fluid and body tissue when the lead is inserted into the living body.

2. The lead of claim 1, wherein the core comprises a metal selected from the group consisting of zirconium and zirconium-containing alloys.

3. The lead of claim 1 or 2, wherein the coating is formed on the surfaces of the core by subjecting the core to a process which results in the in situ formation of the coating.

4. The lead of claim 3, wherein the coating is from about 0.1 to about 20 microns.

5. The lead of claim 2, wherein the core is of zirconium or zirconium-containing alloy and the coating is formed on the surfaces of the core by a process comprising oxidizing the core in air at a temperature that forms diffusion-bonded blue to black zirconium oxides.

6. The lead of claim 1, wherein the coating is from about 0.1 to about 20 microns thick.

7. The lead of claim 1, wherein the coating is deposited on the surfaces of the core by a process selected from the group consisting of physical vapor deposition and chemical vapor deposition.

8. The lead of claim 1, further comprising at least one electrode component that enables the lead to function as a specialized medical application lead, wherein the specialized medical application lead is selected from the group consisting of cardiac pacemaker leads, defibrillator leads, neurological leads, and biological activity monitoring sensor leads.

9. The lead of claim 8, wherein the coating has a thickness of from about 0.1 to about 20 microns.

10. The lead of claim 1, wherein the flexible body further comprises a second coating selected from the group consisting of antibiotics and anticoagulants, wherein said second coating is applied over said corrosion-resistant, biocompatible, durable, stable coating.

11. The lead of claim 1 further comprising an overlay coating over the coating, wherein said overlay coating is applied by a process selected from the group consisting of silver doping and boronation.

12. The lead of claim 1 further comprising overlay coatings over the coating, said overlay coatings selected from the group consisting of amorphous diamond-like carbon, cubic zirconia, and white tetragonal zirconia.

* * * * *

UNITED STATES PATENT AND TRADEMARK OFFICE
CERTIFICATE OF CORRECTION

PATENT NO. : 5,496,359
DATED : March 5, 1996
INVENTOR(S) : James A. Davidson, et. al.

It is certified that error appears in the above-indentified patent and that said Letters Patent is hereby corrected as shown below:

Title page, item [19] line 2, after "Davidson", insert --et al.--.

Title page, item [75], inventor: after "James A. Davidson, Germantown, Tenn.", insert --Catherine M. Asgian, Germantown, Tenn.--

Signed and Sealed this

Eighth Day of April, 1997

Attest:

BRUCE LEHMAN

Attesting Officer

Commissioner of Patents and Trademarks